(12) United States Patent
Tsuchiya et al.

(10) Patent No.: US 7,973,918 B2
(45) Date of Patent: Jul. 5, 2011

(54) APPARATUS AND METHOD FOR PATTERN INSPECTION

(75) Inventors: Hideo Tsuchiya, Tokyo (JP); Takayuki Abe, Kanagawa (JP)

(73) Assignee: NuFlare Technology, Inc., Numazu-shi (JP)

( * ) Notice: Subject to any disclaimer, the term of this patent is extended or adjusted under 35 U.S.C. 154(b) by 0 days.

(21) Appl. No.: 12/552,108

(22) Filed: Sep. 1, 2009

(65) Prior Publication Data

US 2010/0060890 A1    Mar. 11, 2010

(30) Foreign Application Priority Data

Sep. 11, 2008  (JP) ................................ 2008-233023
Aug. 4, 2009  (JP) ................................ 2009-181565

(51) Int. Cl.
*G01N 21/00* (2006.01)
(52) U.S. Cl. ................................. 356/237.1; 356/237.4
(58) Field of Classification Search .... 356/237.1–237.5, 356/394; 382/144, 218; 348/130
See application file for complete search history.

(56) References Cited

U.S. PATENT DOCUMENTS

| | | | | |
|---|---|---|---|---|
| 6,654,110 B2* | 11/2003 | Yonezawa et al. | ......... | 356/237.2 |
| 7,781,749 B2* | 8/2010 | Imai | ............. | 250/503.1 |
| 2003/0081201 A1* | 5/2003 | Shibata et al. | .............. | 356/237.2 |
| 2004/0108448 A1* | 6/2004 | Bosser | ....................... | 250/252.1 |
| 2005/0196059 A1* | 9/2005 | Inoue et al. | .................... | 382/240 |
| 2007/0053583 A1* | 3/2007 | Harabe | ......................... | 382/151 |
| 2009/0040513 A1* | 2/2009 | Abe et al. | .................... | 356/237.5 |
| 2009/0087082 A1 | 4/2009 | Abe et al. | | |

FOREIGN PATENT DOCUMENTS

| | | | |
|---|---|---|---|
| JP | 05-076005 | * | 3/1993 |
| JP | 2004-101438 | | 4/2004 |
| JP | 2007093317 A | * | 4/2007 |

* cited by examiner

*Primary Examiner* — Hoa Q Pham
(74) *Attorney, Agent, or Firm* — Oblon, Spivak, McClelland, Maier & Neustadt, L.L.P.

(57) ABSTRACT

A pattern inspection apparatus includes a pulsed light source configured to emit pulsed light; a stage configured to mount thereon an inspection target object with a pattern formed thereon; a time delay integration (TDI) sensor configured to detect, a plurality of times with a time delay, each pixel value of an optical image of the inspection target object, wherein the optical image is acquired by emitting the pulsed light onto the inspection target object, and to integrate a detected each pixel value for each pixel of the optical image; a light quantity sensor configured to detect a light quantity of the pulsed light after emitting the pulsed light onto the inspection target object; a light quantity measurement circuit configured to input the light quantity detected by the light quantity sensor, and to measure a light quantity of each pulse while being synchronized with a period of the pulsed light; a correction unit configured to input the light quantity of each pulse and an integrated pixel value output from the TDI sensor, and to correct the integrated pixel value output from the TDI sensor, for each pixel of the optical image, using a total light quantity of the light quantity of corresponding each pulse; and an inspection unit configured to inspect whether there is a defect of the pattern, using the integrated pixel value corrected.

4 Claims, 9 Drawing Sheets

APPARATUS AND METHOD FOR PATTERN INSPECTION

CROSS-REFERENCE TO RELATED APPLICATION

This application is based upon and claims the benefit of priority from the prior Japanese Patent Application No. 2008-233023 filed on Sep. 11, 2008 in Japan, and prior Japanese Patent Application No. 2009-181565 filed on Aug. 4, 2009 in Japan, the entire contents of which are incorporated herein by reference.

BACKGROUND OF THE INVENTION

1. Field of the Invention

The present invention relates to a pattern inspection apparatus and a pattern inspection method. For example, it relates to an apparatus and method for inspecting patterns by using pulsed light and a time delay integration (TDI) sensor.

2. Description of Related Art

In recent years, with high integration and large capacity of large scale integrated (LSI) circuits, the line width (critical dimension) required for circuits of a semiconductor element is becoming narrower and narrower. The semiconductor element is manufactured by exposing (transferring) a pattern onto a wafer to form a circuit by a reduced projection exposure apparatus, known as a stepper, while using an original or "master" pattern with a circuit pattern formed thereon. (The original pattern is also called a mask or a reticle, and hereinafter generically referred to as a mask). Therefore, in manufacturing a mask for transferring such a fine circuit pattern onto a wafer, a pattern writing apparatus using electron beams capable of writing or "drawing" fine circuit patterns needs to be employed. Pattern circuits may be written directly onto a wafer by the pattern writing apparatus. In addition to the writing apparatus using electron beams, a laser beam writing apparatus which uses laser beams for writing patterns is also under development.

Since the LSI manufacturing requires a tremendous amount of manufacturing cost, it is crucial to improve its yield. However, as represented by a 1 gigabit DRAM (Dynamic Random Access Memory), the order of a pattern constituting an LSI has been changing from submicron to nanometer dimensions. One of major factors that decrease the yield of the LSI manufacturing is a pattern defect of a mask used when exposing (transferring) a fine pattern onto a semiconductor wafer by the photolithography technology. In recent years, with miniaturization of an LSI pattern formed on a semiconductor wafer, dimensions of defects to be detected have become extremely small. Thus, a pattern inspection apparatus for inspecting defects of a mask for exposure used in manufacturing LSI needs to be highly accurate.

Meanwhile, with development of multimedia technology, the size of Liquid Crystal Display (LCD) substrates is becoming larger, e.g., 500 mm×600 mm or greater, and the size of a pattern such as a Thin Film Transistor (TFT) or the like formed on the liquid crystal substrate is becoming finer. Therefore, it is increasingly required that an extremely small defect of a pattern should be inspected in a large range. For this reason, development of a pattern inspection apparatus which efficiently and short-timely inspects defects of a pattern of a large area LCD and a photomask used in manufacturing the large area LCD is urgently required.

As an inspection method, it is known that an optical image of a pattern formed on a target object or "sample", such as a lithography mask, imaged at a predetermined magnification using a magnifying optical system is compared with design data or an optical image of an identical pattern on the target object. For example, the following is known as pattern inspection methods: "die to die inspection" method that compares data of optical images of identical patterns at different positions on the same mask, and "die to database inspection" method that inputs into the inspection apparatus the writing data (design pattern data) converted from pattern-designed CAD data to a format for input to the writing apparatus when writing a pattern on a mask, generates design image data (reference image) based on the input writing data, and compares the generated design image data with an optical image (measurement data) obtained by capturing an image of the pattern. According to the inspection method of the inspection apparatus, a target object is placed on a stage so that a light flux may scan the object by the movement of the stage. Specifically, the target object is irradiated with a light flux from the light source and the illumination optical system. Light transmitted through the target object or reflected therefrom is focused on a sensor through the optical system. An image captured by the sensor is transmitted as measurement data to a comparison circuit. In the comparison circuit, after position alignment of the images, measurement data and reference data are compared in accordance with an appropriate algorithm. If there is no matching between the data, it is judged that a pattern defect exists.

Now, when inspecting a mask with a pattern formed thereon, a light of short wavelength (ultraviolet band) needs to be used as an illumination light in order to inspect an extremely small detect by the inspection apparatus. Conventionally, as an illumination light, there has been used a continuous wave light source which is controlled to have a fixed exposed light by feedbacking the light power. As a sensor for capturing a pattern image on the mask, there has been used a time delay integration (TDI) sensor which time delay integrates pixel values acquired by shifting a two-dimensional area (xy direction) sensor in x direction while being synchronized with the stage. Thus, by using the TDI sensor, the structure is employed in which shortage of sensitivity of the sensor element is compensated by exposing continuous light accumulated for a predetermined number of times. In contrast, there is disclosed a technique in which since fluctuation of exposed light may occur in a continuous wave light source that does not feedback the light power, a light exposure sensor is placed at the light source side to correct fluctuation of output from the TDI sensor by using an exposed light power of irradiating continuous light (refer to, e.g., Japanese Patent Application Laid-open (JP-A) No. 2004-101438).

The light of short wavelength (ultraviolet band) is not limited to the continuous wave light source mentioned above. For example, an ArF excimer laser light can be cited as the light of short wavelength. An excimer laser light source is smaller and more efficient than the conventional continuous wave light source. Therefore, it is expected to load the excimer laser light source as a light source of the inspection apparatus. However, since the excimer laser light is a pulsed light source, it produces luminescence of only a nanosecond (nSec) during a millisecond (mSec). Then, there is a problem when using this pulsed light as an illumination light, under the influence that an exposed light per pulse varies, an accumulated light of the sensor may considerably change even if a plurality of pulses perform irradiation during the time of the TDI sensor being shifted by one pixel. With respect to the continuous light, even if the light power changes, since the irradiation is always performed during the time of the TDI sensor being shifted by one pixel, the accumulated sensor exposure light can be well averaged. On the other hand, with respect to the pulsed light, since the irradiation time of during the shift by one pixel is much shorter than that of continuous light, the exposed light fluctuation of illumination light gives a great influence on it.

As mentioned above, there is a problem that when a pulsed light is used as an illumination light of the inspection apparatus, under the influence that the light power per pulse varies, the accumulated light to the TDI sensor may change larger than the case of using a continuous light.

BRIEF SUMMARY OF THE INVENTION

It is an object of the present invention to provide an inspection apparatus and method capable of correcting an output change of the TDI sensor in the case of using a pulsed light.

In accordance with one aspect of the present invention, a pattern inspection apparatus includes a pulsed light source configured to emit pulsed light, a stage configured to mount thereon an inspection target object with a pattern formed thereon, a time delay integration (TDI) sensor configured to detect, a plurality of times with a time delay, each pixel value of an optical image of the inspection target object, wherein the optical image is acquired by emitting the pulsed light onto the inspection target object, and to integrate a detected each pixel value for each pixel of the optical image, a light quantity sensor configured to detect a light quantity of the pulsed light after emitting the pulsed light onto the inspection target object, a light quantity measurement circuit configured to input the light quantity detected by the light quantity sensor, and to measure a light quantity of each pulse while being synchronized with a period of the pulsed light, a correction unit configured to input the light quantity of each pulse and an integrated pixel value output from the TDI sensor, and to correct the integrated pixel value output from the TDI sensor, for each pixel of the optical image, using a total light quantity of the light quantity of corresponding each pulse, and an inspection unit configured to inspect whether there is a defect of the pattern, using the integrated pixel value corrected.

In accordance with another aspect of the present invention, a pattern inspection apparatus includes a pulsed light source configured to emit pulsed light, a stage configured to mount thereon an inspection target object with a pattern formed thereon, a time delay integration (TDI) sensor configured to detect, a plurality of times with a time delay, each pixel value of an optical image of the inspection target object, wherein the optical image is acquired by emitting the pulsed light onto the inspection target object, and to integrate a detected each pixel value for each pixel of the optical image, a light quantity sensor configured to detect a light quantity of the pulsed light before emitting the pulsed light onto the inspection target object, a light quantity measurement circuit configured to input the light quantity detected by the light quantity sensor, and to measure a light quantity of each pulse while being synchronized with a period of the pulsed light, a correction unit configured to input the light quantity of each pulse and an integrated pixel value output from the TDI sensor, and to correct the integrated pixel value output from the TDI sensor, for each pixel of the optical image, using a total light quantity of the light quantity of corresponding each pulse, and an inspection unit configured to inspect whether there is a defect of the pattern, using the integrated pixel value corrected.

Moreover, in accordance with another aspect of the present invention, a pattern inspection method includes emitting pulsed light, detecting, a plurality of times with a time delay, each pixel value of an optical image of an inspection target object with a pattern formed thereon, wherein the optical image is acquired by emitting the pulsed light onto the inspection target object, and integrating a detected each pixel value for each pixel of the optical image, by using a time delay integration (TDI) sensor, detecting a light quantity of the pulsed light after emitting the pulsed light onto the inspection target object, inputting the light quantity detected and measuring a light quantity of each pulse while being synchronized with a period of the pulsed light, inputting the light quantity of each pulse and an integrated pixel value output from the TDI sensor, and correcting the integrated pixel value output from the TDI sensor, for each pixel of the optical image, using a total light quantity of the light quantity of corresponding each pulse, and inspecting whether there is a defect of the pattern, using the integrated pixel value corrected.

Furthermore, in accordance with another aspect of the present invention, a pattern inspection method includes emitting pulsed light, detecting, a plurality of times with a time delay, each pixel value of an optical image of an inspection target object with a pattern formed thereon, wherein the optical image is acquired by emitting the pulsed light onto the inspection target object, and integrating a detected each pixel value for each pixel of the optical image, by using a time delay integration (TDI) sensor, detecting a light quantity of the pulsed light before emitting the pulsed light onto the inspection target object, inputting the light quantity detected and measuring a light quantity of each pulse while being synchronized with a period of the pulsed light, inputting the light quantity of each pulse and an integrated pixel value output from the TDI sensor, and correcting the integrated pixel value output from the TDI sensor, for each pixel of the optical image, using a total light quantity of the light quantity of corresponding each pulse, and inspecting whether there is a defect of the pattern, using the integrated pixel value corrected.

DETAILED DESCRIPTION OF THE INVENTION

Embodiment 1

Figure 1:
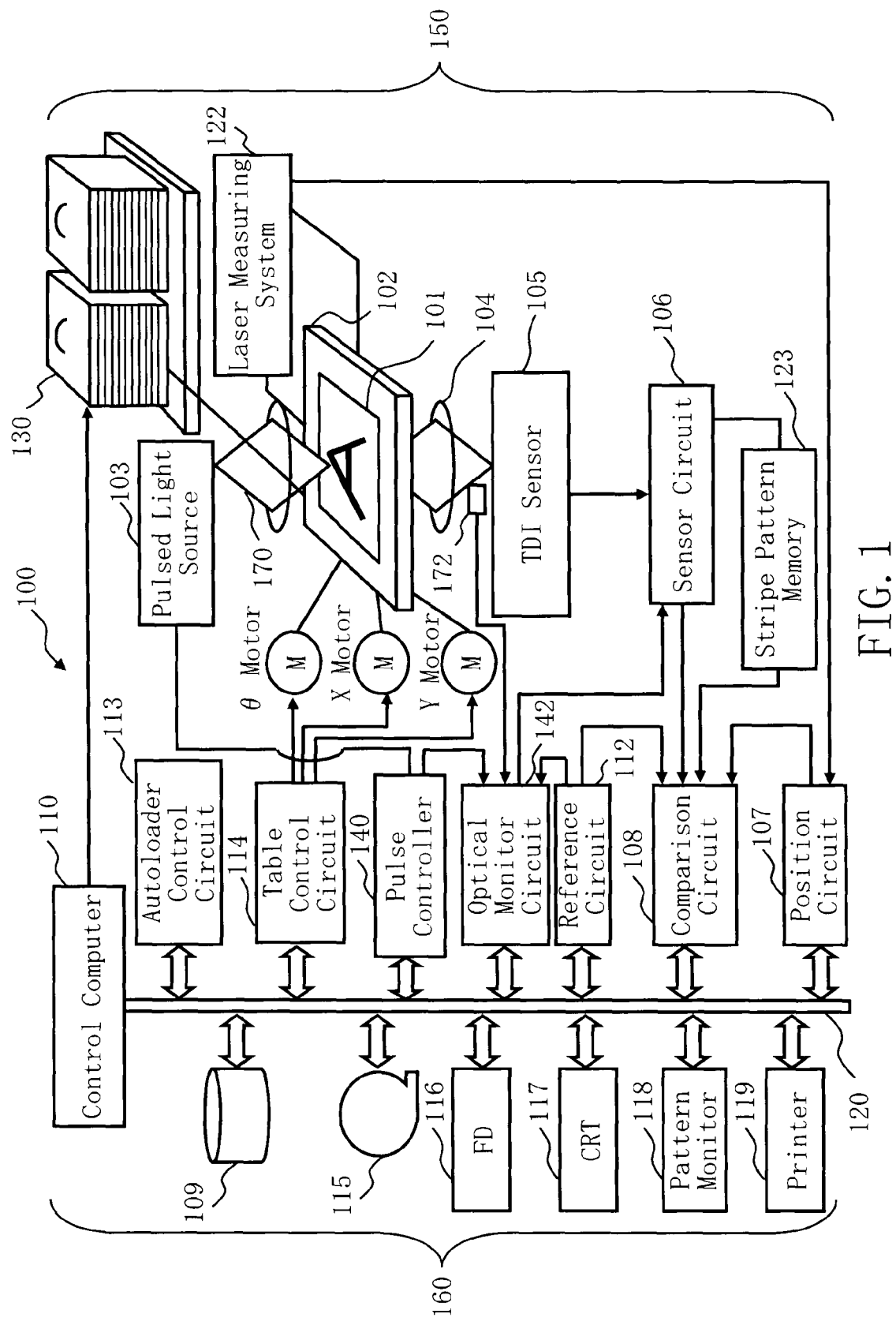
FIG. 1 is a schematic diagram showing the structure of a pattern inspection apparatus according to Embodiment 1.

FIG. 1 is a schematic diagram showing the structure of a pattern inspection apparatus according to Embodiment 1. In FIG. 1, an inspection apparatus 100 which inspects defects of a target object, such as a mask, includes an optical image acquisition unit 150 and a control system circuit 160. The optical image acquisition unit 150 includes a pulsed light source 103, an XYθ table 102, an illumination optical system 170, a magnifying optical system 104, a time delay integration (TDI) sensor 105, a sensor circuit 106, a light exposure sensor 172 (an example of light quantity sensor), a laser measuring system 122, and an autoloader 130. In the control circuit 160, a control computer 110 being a computer is connected, through a bus 120, to a position circuit 107, a comparison circuit 108, a reference circuit 112, an autoloader control circuit 113, a table control circuit 114, a pulse controller 140, a light exposure monitor circuit 142 (an example of light quantity monitor circuit), a magnetic disk drive 109, a magnetic tape drive 115, a flexible disk drive (FD) 116, a CRT 117, a pattern monitor 118, and a printer 119. The light exposure sensor 172 is located before the TDI sensor 105, where a quantity of light having passed through the XYθ table 102 and before entering the TDI sensor can be detected. The sensor circuit 106 is connected to a stripe pattern memory 123 which is connected to a comparison circuit 108. The XYθ table 102 is driven by an X-axis motor, a Y-axis motor, and a θ-axis motor. The XYθ table 102 serves as an example of the stage. FIG. 1 depicts structure elements necessary for describing Embodiment 1, and it should be understood that other structure elements generally necessary for the inspection apparatus 100 may also be included therein.

In the inspection apparatus 100, an inspection optical system of large magnification is composed of the pulsed light source 103, the XYθ table 102, the illumination optical system 170, the magnifying optical system 104, the TDI sensor 105, the light exposure sensor 172, and the sensor circuit 106. The XYθ table 102 is driven by the table control circuit 114 under the control of the control computer 110. The XYθ table 102 can be moved by a drive system such as a three-axis (X-Y-θ) motor, which drives the XYθ table 102 in the X direction, the Y direction, and the θ direction. For example, a step motor can be used as each of these X, Y, and θ motors. The moving position of the XYθ table 102 is measured by the laser measuring system 122 and supplied to the position circuit 107. A photomask 101 on the XYθ table 102 is automatically conveyed from the autoloader 130 driven by the autoloader control circuit 113, and automatically ejected after the inspection.

The photomask 101 serving as an inspection target object is placed on the XYθ table 102 movable in a horizontal direction and a rotating direction by the X-, Y-, and θ-axis motors. The photomask 101 has a pattern formed thereon. Then, the pattern written on the photomask 101 is irradiated by a pulsed light of a wavelength of the ultraviolet band, such as the ArF excimer laser light, emitted from the pulsed light source 103, such as the ArF excimer laser light source, through the illumination optical system 170. The emission timing (period) of the pulsed light source 103 is controlled by the pulse controller 140. The light transmitted through the photomask 101 is focused on the TDI sensor 105 through the magnifying optical system 104, as an optical image and enters in it. On this occasion, a quantity of light having passed through the photomask 101 and before entering the TDI sensor is detected by the light exposure sensor.

Figure 2:
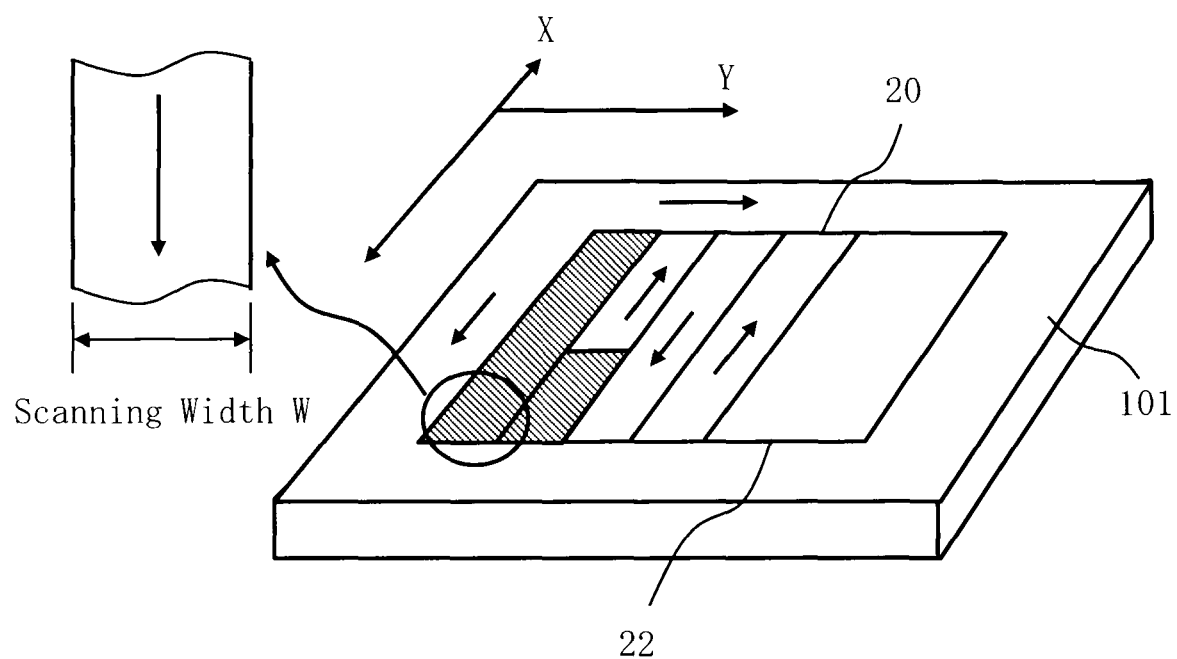
FIG. 2 is a schematic diagram describing a procedure for acquiring an optical image according to Embodiment 1.

FIG. 2 is a schematic diagram describing a procedure for acquiring an optical image according to Embodiment 1. An inspection region 22 is virtually divided into a plurality of strip-like inspection stripes 20, each having a scanning width W, in the Y direction, for example. The operation of the XYθ table 102 is controlled so that each divided inspection stripe 20 may be continuously scanned. By the movement of the XYθ table 102, optical images are acquired by the TDI sensor 105 which relatively moves in the X direction (first direction) continuously. That is, the TDI sensor 105 continuously captures optical images each having a scanning width W as shown in FIG. 2. It should be understood that the TDI sensor moves relatively to the movement of the XYθ table 102. According to Embodiment 1, after capturing an optical image in one inspection stripe 20, the TDI sensor 105 similarly captures another optical image having the scanning width W continuously at a position shifted in the Y direction by a scanning width W, while moving in a direction reverse to the last image capturing direction. That is, the image capturing is repeated in the forward (FWD) and backward (BWD) direction, meaning going in a reverse direction when advancing and returning.

The pattern image focused on the TDI sensor 105 is photoelectrically converted by each light receiving element of the TDI sensor 105, and further analog-to-digital (A/D) converted by the sensor circuit 106. Pixel data of each inspection stripe 20 is stored in the stripe pattern memory 123. Then, the pixel data is sent to the comparison circuit 108, with data indicating the position of the photomask 101 on the XYθ table 102, output from the position circuit 107. The pixel data of measurement data is 8-bit unsigned data, for example, and indicates a gray level (light intensity, or "light quantity") of brightness of each pixel.

Figure 3:
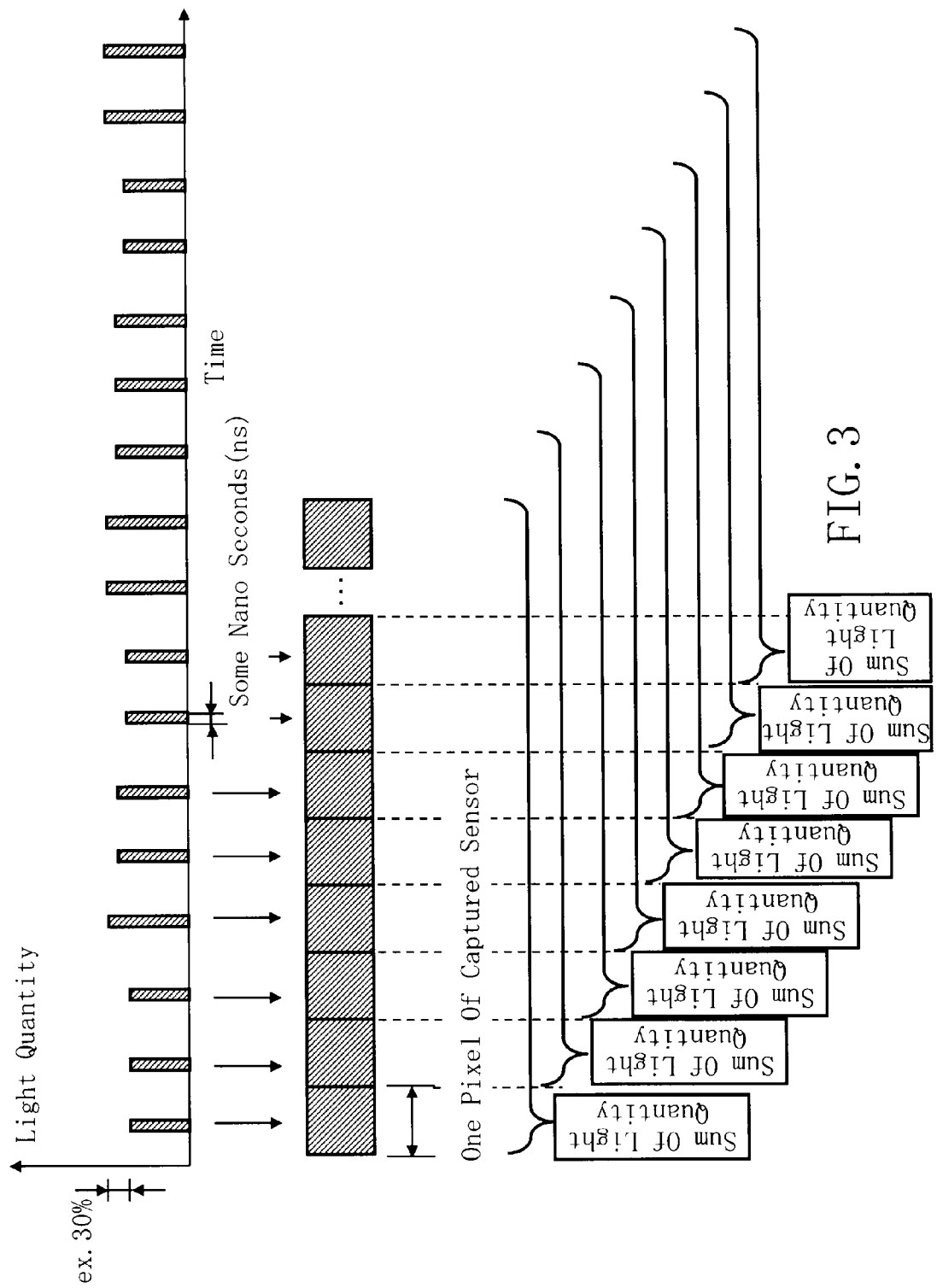
FIG. 3 is a schematic diagram showing an example of a synchronous relation between a pulse emission timing and a TDI sensor light-receiving element according to Embodiment 1.

FIG. 3 is a schematic diagram showing an example of a synchronous relation between the pulse emission timing and the TDI sensor light-receiving element according to Embodiment 1. In order to acquire a pixel value being a luminance or "brightness" value of one pixel of an optical image, the TDI sensor 105 receives light while shifting sensor pixels of sixteen rows (light-receiving elements) one-pixel by one-pixel, and outputs an accumulated (integrated) value of values received by the sensor pixels of sixteen rows. Thus, the TDI sensor 105 detects each pixel value of the optical image of the photomask 101 a plurality of times with a time delay, and accumulates (integrates) each detected pixel value (pulse intensity: t1, t2, . . . , tn) for each pixel of the optical image. This accumulated value becomes a pixel value of one pixel of the optical image. FIG. 3 shows the case where the pulsed light source 103 emits one pulse of light, for example, when the TDI sensor 105 relatively shifts by one sensor pixel. As shown in FIG. 3, there is variation in the light intensity(or "light quantity") of the emitted pulsed light, and the variation is about 30%, for example. For this reason, under the influence of such light intensity fluctuation, the accumulated value of the sensor pixels of sixteen rows will also change.

Then, in Embodiment 1, the intensity of pulsed light received by the TDI sensor 105 is measured for each pulse by the light exposure sensor 172 and the light exposure monitor circuit 142. The light exposure monitor circuit 142 (light quantity measurement circuit) acquires information on emission timing (period) from the pulse controller 140, and receives (inputs) the light exposure (or "light quantity") detected by the light exposure sensor 172 while being synchronized with the period of the pulsed light. The light exposure monitor circuit 142 converts the light quantity data into digital data after measuring a light intensity of each pulse. The measured light intensity of each pulse is output to the sensor circuit 106. Then, in the sensor circuit 106, for each pixel of the optical image, an accumulated value output from the TDI sensor 105 is corrected based on the sum of light intensities (total light quantity) of the corresponding pulsed light.

Figure 4:
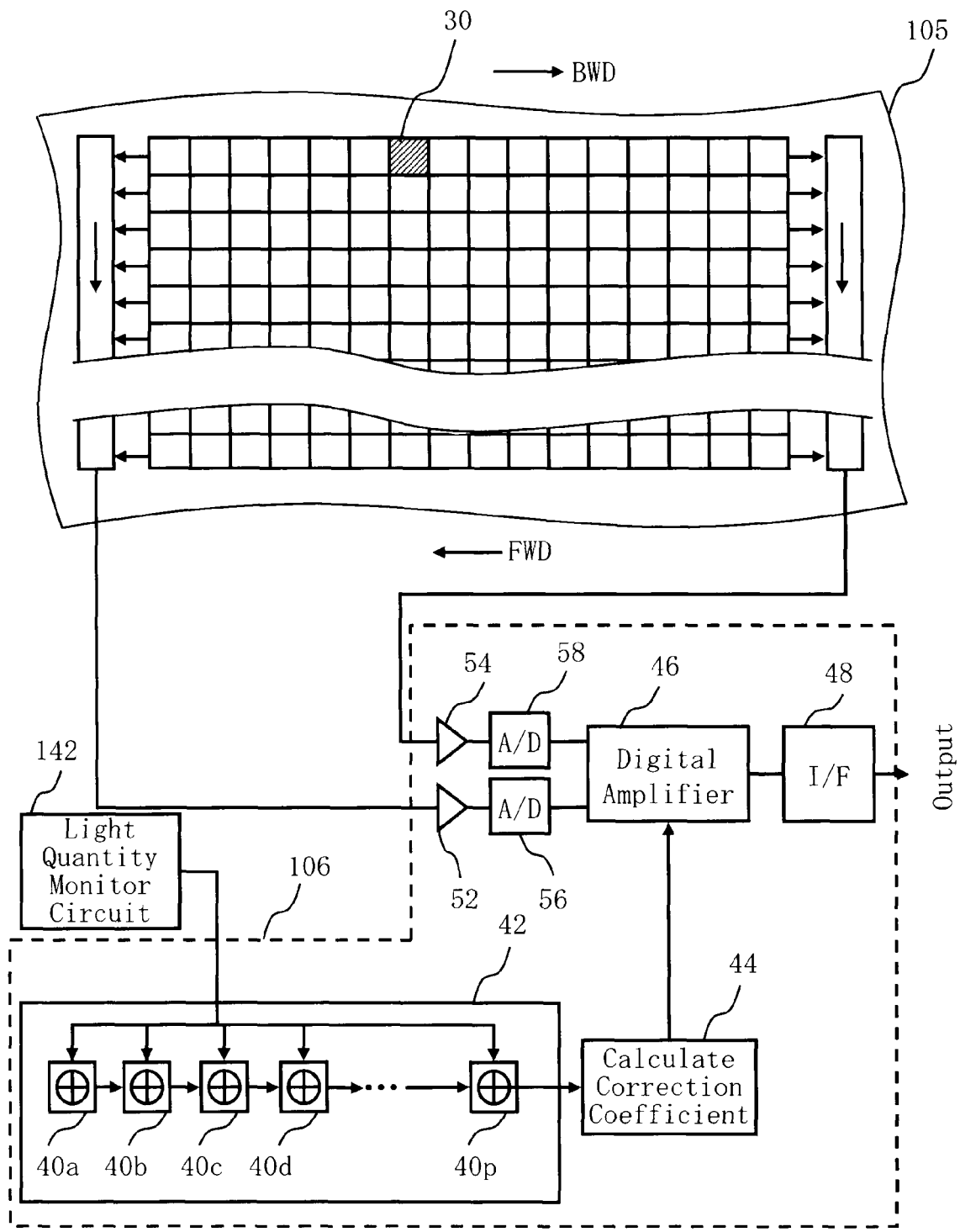
FIG. 4 is a schematic diagram showing the internal structure of a sensor circuit according to Embodiment 1.

FIG. 4 is a schematic diagram showing the internal structure of the sensor circuit according to Embodiment 1. When the TDI sensor 105 relatively moves in the forward direction (FWD), the sensor circuit 106 inputs an accumulated or "integrated" value (analog data) of pixel values of the sensor pixels 30 of a required number of rows (for example, sixteen rows) corresponding to one pixel of the optical image. In other words, the TDI sensor 105 outputs the accumulated value (integrated pixel value), and the sensor circuit 106 inputs the accumulated value output by the TDI sensor 105. The amplifier 52 amplifies the input accumulated value in the sensor circuit 106. The analog digital (A/D) converter 56 converts the analog data having been amplified by the amplifier 52 into digital data and outputs it to the digital amplifier 46.

When the TDI sensor 105 relatively moves in the backward direction (BWD), the sensor circuit 106 inputs an accumulated value (analog data) of pixel values of the sensor pixels 30 of a required number of rows (for example, sixteen rows) corresponding to one pixel of the optical image. In other words, the TDI sensor 105 outputs the accumulated value (integrated pixel value), and the sensor circuit 106 inputs the accumulated value output by the TDI sensor 105. The amplifier 54 amplifies the input accumulated value in the sensor circuit 106. The analog digital (A/D) converter 58 converts the analog data having been amplified by the amplifier 54 into digital data and outputs it to the digital amplifier 46. Moreover, the sensor circuit 106 inputs the measured light quantity of each pulse from the light exposure monitor circuit 142 one by one. In the sensor circuit 106, an accumulating circuit 42 integrates (accumulatedly adds) light intensities of pulsed light of the number of pulses received by the sensor pixels 30 of a required number of rows (for example, sixteen rows) corresponding to one pixel of the optical image, and outputs the integrated total light quantity to the correction coefficient calculation unit 44. In the accumulating circuit 42, there are arranged shift registers 40 of a required number of rows (for example, sixteen rows) of the sensor pixels 30 corresponding to one pixel of the optical image. The accumulation method in the accumulating circuit 42 will be described in detail later.

The light quantity detected by the light exposure sensor 172 and observed by the light exposure monitor circuit 142 changes depending upon the shape density of a measurement pattern. However, an ideal total light amount Ti (reference total light quantity) in a certain observation region can be calculated from pattern density, and transmittance/reflectance of the inspection mask, etc. using pattern data generated by the reference circuit 112 based on the design pattern data of the region.

In the correction coefficient calculation unit 44, in preparation for that the total light amount T accumulated by the accumulating circuit 42 changes from the ideal total light amount Ti, a correction coefficient Ti/T is calculated and output to the digital amplifier 46. The digital amplifier 46 (correction unit) corrects a pixel value (accumulated value or "integrated pixel value") output from the TDI sensor 105, for each pixel of the optical image, using the total light amount T of light intensity for each corresponding pulse. That is, the digital amplifier 46 multiplies the accumulated value from the TDI sensor 105 by a corresponding correction coefficient Ti/T, for each pixel of the optical image. By performing the multiplication, it is possible to perform correction of equalization of the output level of the TDI sensor 105, which fluctuates because of the exposed light fluctuation of each pulse. The pixel value after the correction is output to the stripe pattern memory 123 through the interface (I/F) circuit 48.

Figure 5:
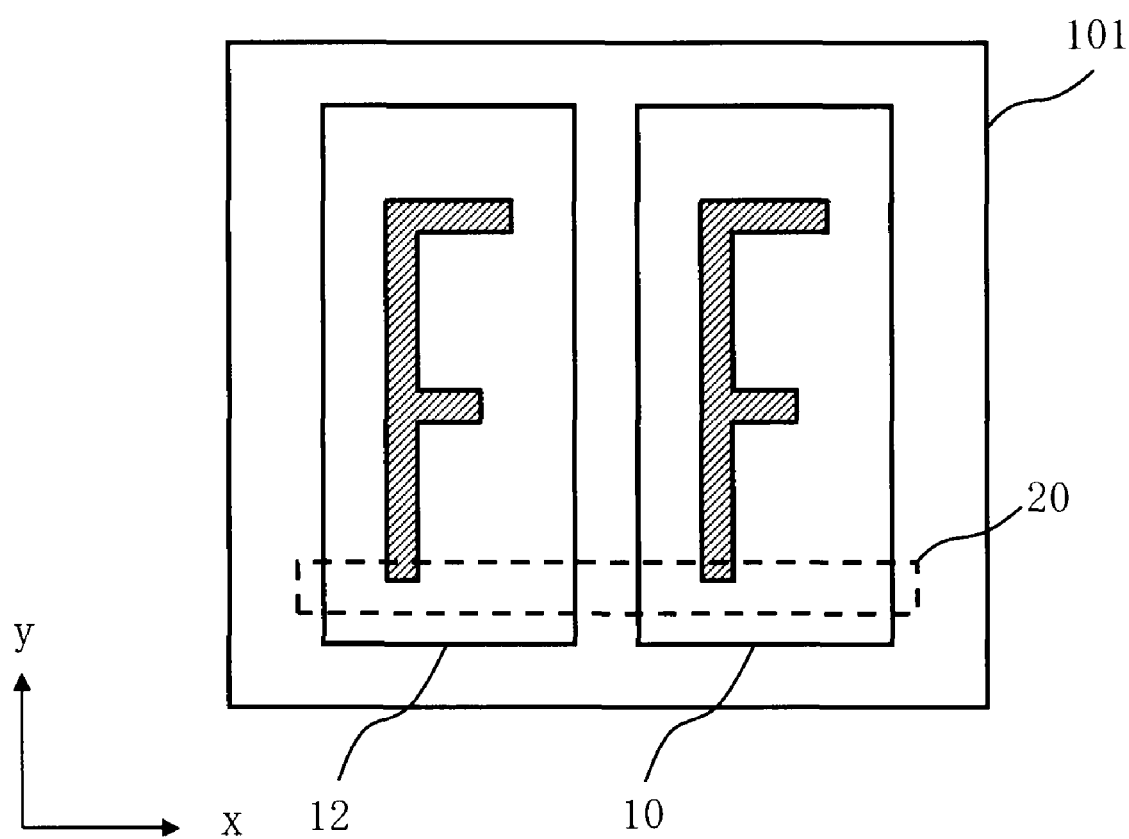
FIG. 5 shows an example of a photomask to be inspected by a die-to-die method according to Embodiment 1.

FIG. 5 shows an example of a photomask to be inspected by the die-to-die method according to Embodiment 1. In FIG. 5, it is a premise that there are two or more inspection regions (die) written with the same design data in the photomask 101. In FIG. 5, there are two regions written based on the same design data: an inspection region 10 and an inspection region 12 in the photomask 101. At this point, when performing the die-to-die inspection, the entire inspection region including these two inspection regions 10 and 12 is virtually divided into a plurality of strip-like inspection stripes 20, each having a scanning width W, in the Y direction, for example, as shown in FIG. 2. Therefore, the two corresponding regions are included in one inspection stripe 20. Then, the operation of the XYθ table 102 is controlled so that each divided inspection stripe 20 may be scanned continuously.

The die-to-die inspection is performed as follows: After measurement data of the inspection regions 10 and 12 imaged together is stored in the stripe pattern memory 123 for each inspection stripe 20, it is sent to the comparison circuit 108 (inspection unit), with data indicating the position of the photomask 101 on the XYθ table 102 output from the position circuit 107. Then, an image of the size of the inspection stripe is cut into an inspection image of the size of 512×512 pixels, for example. Position alignment of the inspection images of corresponding regions of the inspection regions 10 and 12 is performed. Pixel data of each inspection image is compared with each other for each pixel according to a predetermined algorithm, to judge whether there is a defect of a pattern or not. The compared result is output, for example, to the magnetic disk drive 109, magnetic tape drive 115, FD 116, CRT 117, pattern monitor 118, or printer 119. Alternatively, it may be output outside.

Figure 6A:
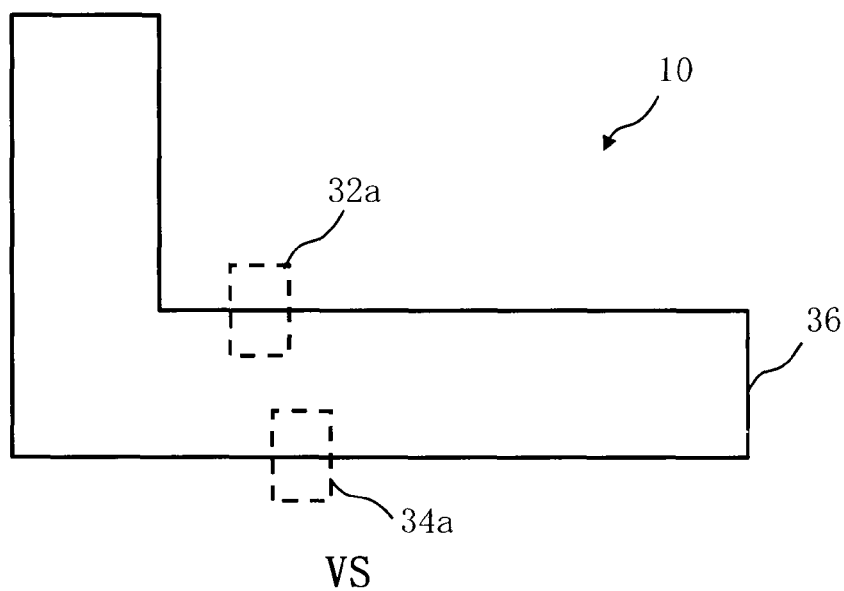
FIGS. 6A to 6C illustrate an effect of light power correction in the case of a die-to-die inspection according to Embodiment 1.
Figure 6B:
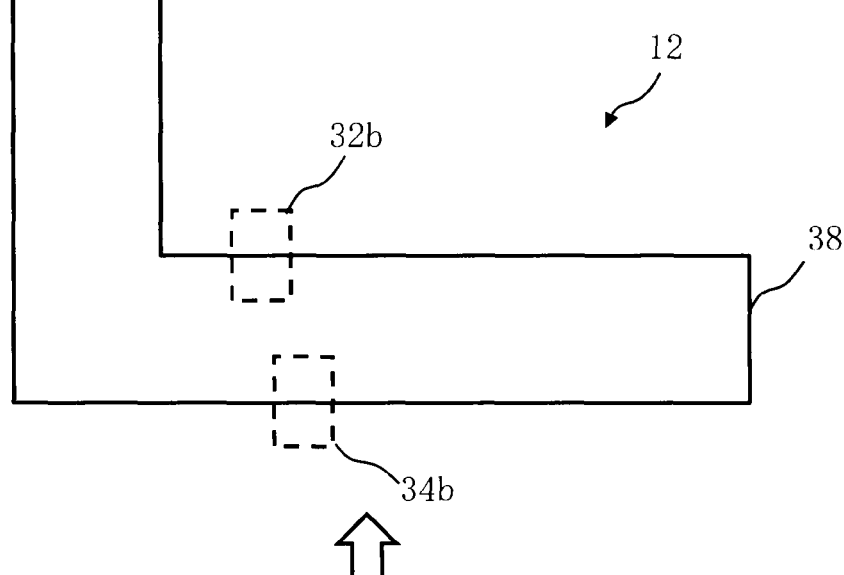
Figure 6C:
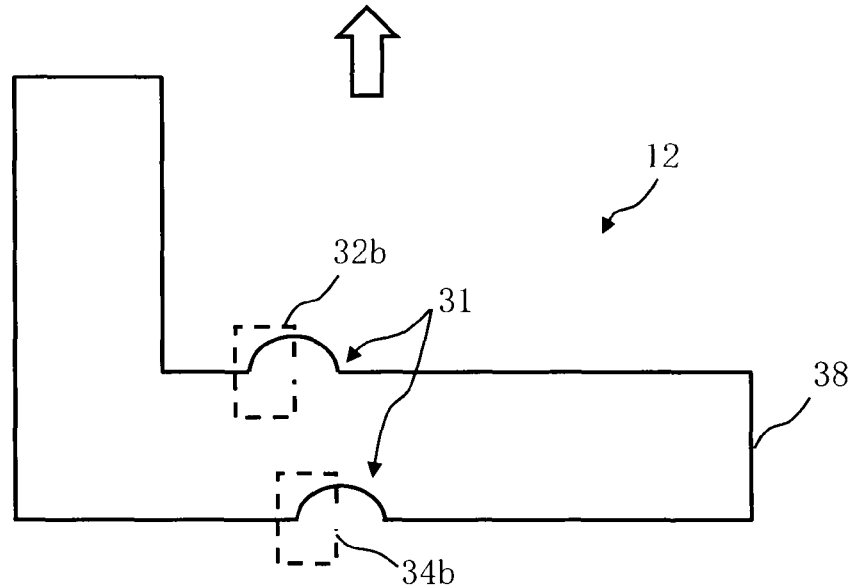

FIGS. 6A to 6C illustrate the effect of the light power (or "light quantity") correction in the case of the die-to-die inspection according to Embodiment 1. In FIGS. 6A to 6C, if there is a light power fluctuation of pulsed light when imaging the inspection region 12, namely, one of the two regions, the imaged pattern 38 appears as if it had pattern deformations 31 at a pixel 32*b* and a pixel 34*b* because of the output change of the sensor pixel, as shown in FIG. 6C. On the other hand, if there is no light power fluctuation of pulsed light when imaging the region 10, namely the other of the two regions, the imaged pattern 36 has no pattern deformation at corresponding pixels 32*a* and 34*a*, as shown in FIG. 6A. Therefore, if comparison is performed as they are, it will be misjudged that there are defects in a pixel 32 and a pixel 34. However, according to Embodiment 1, since the output change of the sensor pixel is corrected using the total light power(or "total light quantity") as mentioned above, the pattern deformations 31 at the corresponding pixels 32*b* and 34*b* are corrected in the imaged pattern 38 as shown in FIG. 6B. Therefore, even when they are compared, the misjudgment being a defect can be prevented.

The die-to-database inspection is performed as follows: The comparison circuit 108 (inspection unit) inputs pixel data from the stripe pattern memory 123 for each inspection stripe 20. On the other hand, the reference circuit 112 reads design data from the magnetic disk unit 109 through the control computer 110. The read design data of the photomask 101 is converted into image data of binary values or multiple values to generate reference data (reference image). Then, the reference data is sent to the comparison circuit 108 (inspection unit).

Position alignment is performed between the measurement data and the reference data. Then, each pixel data of the measurement data and reference pixel data of the reference data are compared for each pixel according to a predetermined algorithm, and existence of a defect is judged based on the comparison result. Then, the comparison result is output, for example, to the magnetic disk drive 109, magnetic tape drive 115, FD 116, CRT 117, pattern monitor 118, or printer 119. Alternatively, it may be output to the outside.

If regarding the pattern 36 shown in FIG. 6A as a pattern of the reference image, the same effect as that of the die-to-die inspection case can also be attained in the die-to-database inspection.

In the case of light transmitted through the photomask 101 being received by the TDI sensor 105 as shown in FIG. 1, it is acceptable that the ideal accumulated light (or "ideal accumulated light quantity") of the TDI sensor 105 is even smaller than that in the case of reflected light being received. Therefore, in Embodiment 1, it is shown the case where when the TDI sensor 105 relatively moves by one sensor pixel, the pulsed light source 103 emits one pulse of light, for example, as shown in FIG. 3, but, it is not limited thereto. That is, according to Embodiment 1, it is not limited to receiving the light transmitted through the photomask 101 by the TDI sensor 105, and thus receiving the light reflected from the photomask 101 is also acceptable. However, in the case of receiving the light reflected from the photomask 101, the mask may be made of a material having reflectance efficiency inferior to transmittance efficiency. In such a case, it is preferable for the ideal accumulated light of the TDI sensor 105 to be larger than that in the case of receiving the transmitted light. Therefore, for example, when the TDI sensor 105 relatively moves by one sensor pixel, it is preferable for the pulsed light source 103 to emit two pulses of light, for example. Alternatively, it may emit three or more pulses of light.

As mentioned above, it is preferable for the number of pulses of each pixel value detected by the TDI sensor 105 to be variable depending upon the structure of the optical system used and the material of the photomask 101 used. Then, in accordance with the variable number of pulses of each pixel value, the total light amount T accumulated by the accumulating circuit 42 becomes variable.

For example, in the case the pulsed light source 103 emits one pulse of light when the TDI sensor 105 relatively moves by one sensor pixel, the number of sensor pixels of the TDI sensor 105 used for acquiring a value of one pixel of the optical image accords with the number of pulses of light power used for the total light amount T. Moreover, in the case the pulsed light source 103 emits two pulses of light when the TDI sensor 105 relatively moves by one sensor pixel, the number of pulses of light power used for the total light amount T is twice as many as the number of sensor pixels of the TDI sensor 105 used for acquiring a value of one pixel of the optical image. Similarly, if three pulses of light is emitted, it becomes three times. Thus, it is preferable for the number of pulses of light power used for the total light amount T to be an integral multiple of the number of pixel values (the number of sensor pixels per pixel) integrated by the TDI sensor 105.

Figure 7:
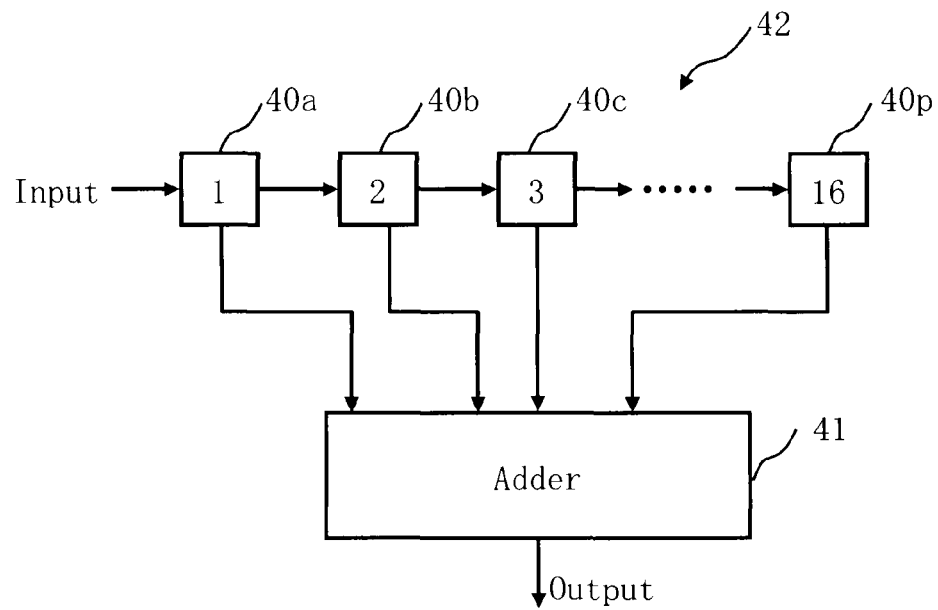
FIG. 7 is a schematic diagram showing an example of the internal structure of an accumulating circuit according to Embodiment 1.

FIG. 7 is a schematic diagram showing an example of the internal structure of the accumulating circuit according to Embodiment 1. In the accumulating circuit 42 in the sensor circuit 106, shift registers 40a to 40p of the number of required rows (for example, sixteen rows) of the sensor pixels 30 corresponding to one pixel of the optical image, and an adder 41 are arranged. Light intensity measured at each pulse is transmitted in order from the shift register 40a of the first row to the shift register 40p of the sixteenth row, for example. Then, the light intensity value temporarily stored in each shift register 40 is sent to the adder 41 at the pulse period, and the light quantity is accumulatedly added each time to calculate the total light amount T. Thus, the total light amount T is calculated at the pulse period, and the calculated total light amount T is output one by one at the pulse period. While only one adder 41 is shown in FIG. 7, since it is usually difficult to simultaneously input sixteen values to add, it may be sufficient to perform the calculation by combining a plurality of two-input adders as the internal structure of the adder 41. The internal structure of the accumulating circuit 42 is not limited to the one in FIG. 7.

Figure 8:
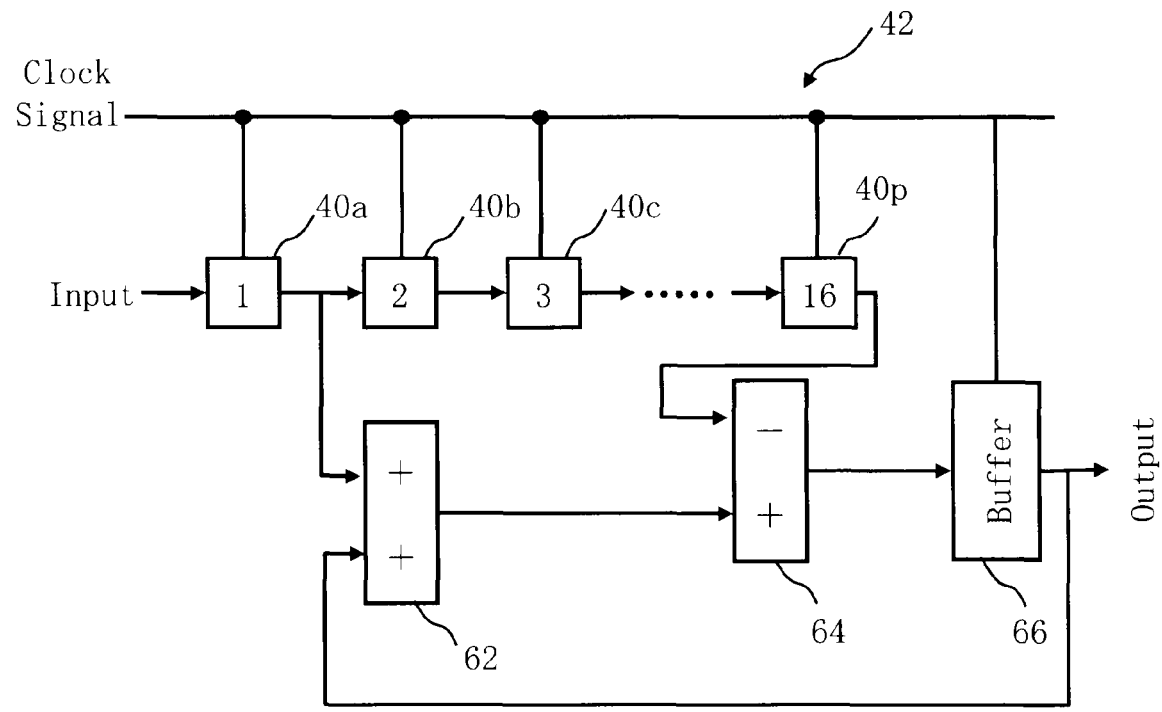
FIG. 8 is a schematic diagram showing another example of the internal structure of the accumulating circuit according to Embodiment 1.

FIG. 8 is a schematic diagram showing another example of the internal structure of the accumulating circuit according to Embodiment 1. In the accumulating circuit 42 in the sensor circuit 106, the shift registers 40a to 40p of the number of required rows (for example, sixteen rows) of the sensor pixels 30 corresponding to one pixel of the optical image, an adder 62, a subtractor 64, and a register 66 are arranged. Light intensity measured at each pulse is transmitted in order from the shift register 40a of the first row to the shift register 40p of the sixteenth row, for example. Then, the light intensity value temporarily stored in the shift register 40a of the first row and the light quantity stored in the register 66 are sent to the adder 62 at the pulse period, and the light quantity is added each time. The subtractor 64 inputs an additional value added by the adder 62 to the positive electrode (+) side, and a light intensity value temporarily stored in the shift register 40p of the last row (for example, the sixteenth row) to the negative electrode (−) side, and subtracts the value at the negative electrode (−) side from the value at the positive electrode (+) side. The output of the subtractor 64 is stored in the register 66 and output one by one as the total light amount T at the pulse period. Unlike FIG. 7, it is sufficient to have one adder 62 and one subtractor 64 in the structure of FIG. 8. Therefore, as mentioned above, even when the number of pulses used for the total light amount T is variable, such as the case of the number of required pulses for the reflection system and the transmission system being different, what is necessary is just to increase or decrease the number of shift registers 40, thus being more preferable. The internal structure of the accumulating circuit 42 is not limited to the one in FIG. 8.

Figure 9:
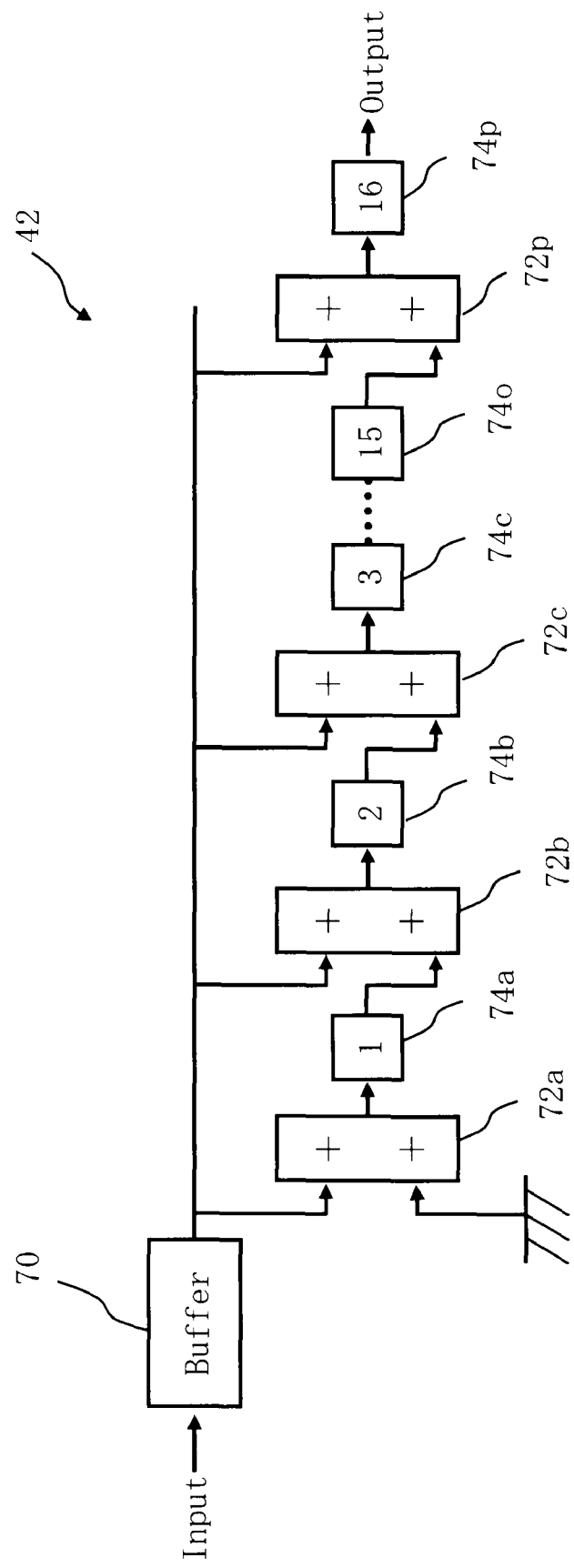
FIG. 9 is a schematic diagram showing another example of the internal structure of the accumulating circuit according to Embodiment 1.

FIG. 9 is a schematic diagram showing another example of the internal structure of the accumulating circuit according to Embodiment 1. In the accumulating circuit 42 in the sensor circuit 106, shift registers 74a to 74p of the number of required rows (for example, sixteen rows) of the sensor pixels 30 corresponding to one pixel of the optical image, adders 72a to 72p of the same number as the shift registers 74, and a register 70 are arranged. The light intensity of the first pulse, temporarily stored in the register 70, is input to an input terminal of the adder 72a of the first row, where the other terminal is earth-grounded. An additional value in the adder 72a is temporarily stored in the shift register 74a of the first row. Then, the light intensity of the second pulse, temporarily stored in the register 70, is input to an input terminal of the adder 72b of the second row, and the value stored in the shift register 74a of the first row is input to the other terminal. An additional value in the adder 72b is temporarily stored in the shift register 74b of the second row. Thus, cascade adding is performed one by one to the last row, and the value stored in the shift register 74p of the last row (for example, the sixteenth row) is output one by one as the total light amount T at the pulse period.

According to Embodiment 1, as mentioned above, the TDI sensor 105 images an optical image of an inspection target object, that is a target object to be inspect, wherein the optical image is obtained from the inspection target object irradiated by a pulsed light. At this point, the change of output strength of the TDI sensor 105 produced by the light power change of pulsed light can be corrected by a correction coefficient using the total of the light quantity detected by the light exposure sensor 172 at the TDI sensor 105 side. While the transmittance and the reflectance change depending upon material of the film surface of the inspection target object, an actual light amount received by the TDI sensor 105 can be corrected by detecting a light amount at the TDI sensor 105 side by the light exposure sensor 172.

Embodiment 2

Although the amount (or "quantity") of light transmitted through the inspection target object or reflected therefrom, that is the light before entering the TDI sensor 105, is measured in Embodiment 1, it is not limited thereto. Now, in Embodiment 2, the structure in which the amount of light before transmitting through the photomask 101 is detected by the light exposure sensor will be described.

Figure 10:
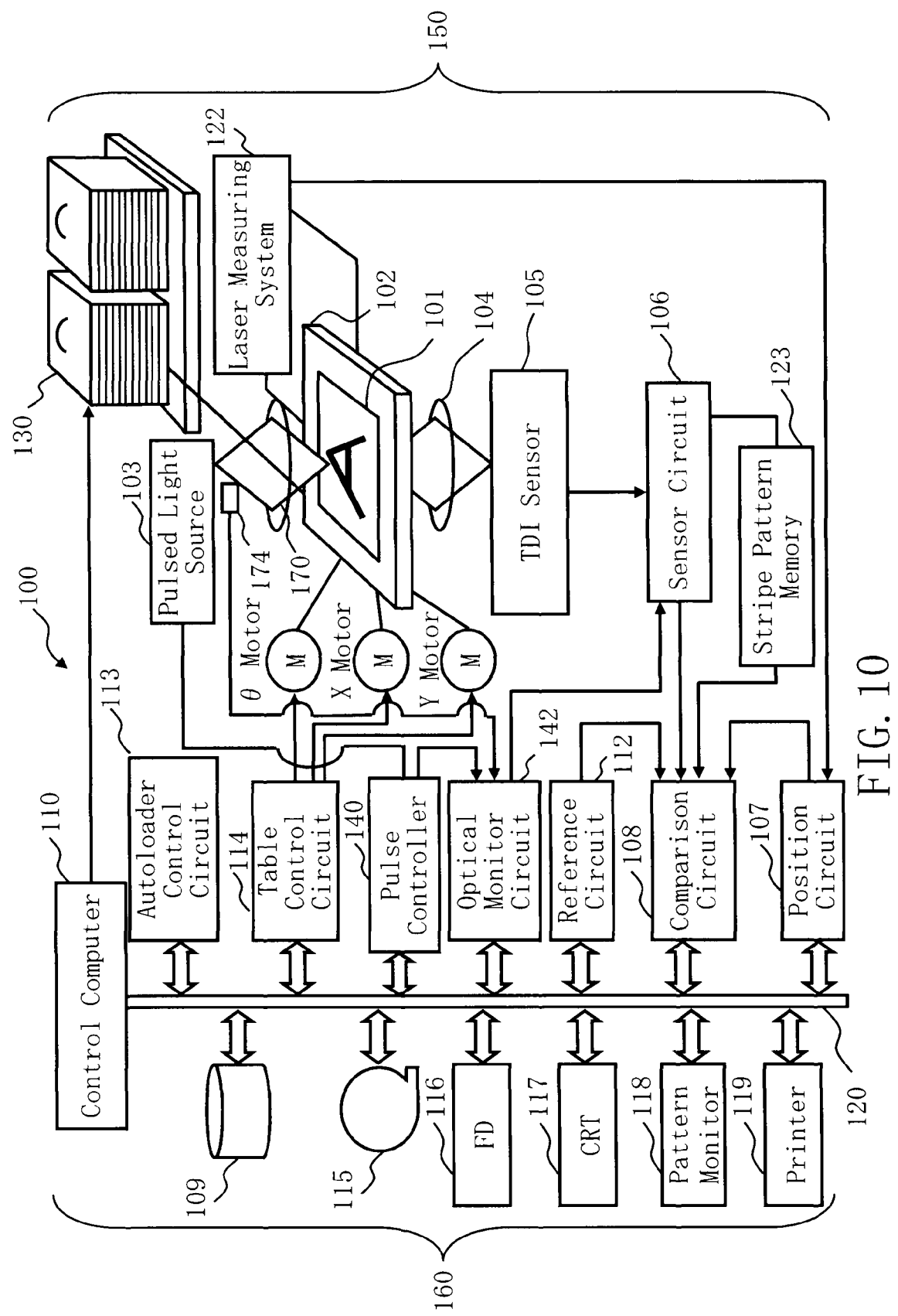
FIG. 10 is a schematic diagram showing the structure of a pattern inspection apparatus according to Embodiment 2.

FIG. 10 is a schematic diagram showing the structure of a pattern inspection apparatus according to Embodiment 2. FIG. 10 is the same as FIG. 1 except for a light exposure sensor 174, instead of the light exposure sensor 172, being arranged at the pulsed light source 103 side. That is, the light exposure sensor 174 is arranged at the position where a light intensity of pulsed light before irradiating the photomask 101 on the XYθ table 102 can be detected. In addition, according to Embodiment 2, since the amount of light before transmitting through the inspection pattern is monitored by the light exposure sensor 174, the ideal total light amount Ti (reference total light quantity) does not depend on the pattern. Therefore, as an ideal total light amount Ti in Embodiment 2, a light quantity applicable as a sufficient stable ideal light amount is monitored and held before the inspection start, to be prepared for a pulsed light intensity change during the inspection. Other structure and operations of the pattern inspection apparatus 100 are the same as those in Embodiment 1.

According to Embodiment 2, as mentioned above, the TDI sensor 105 images an optical image of the inspection target object, obtained by being irradiated by a pulsed light. At this point, the change of output strength of the TDI sensor 105 produced by the light intensity change of pulsed light can be corrected by a correction coefficient using the total of the light amount detected by the light exposure sensor 172 at the pulsed light source 103 side. By detecting the light amount (or "light quantity") at the side of the pulsed light source 103 side by using the light exposure sensor 172, it becomes possible to eliminate the influence of the change of the light amount of transmitted light or reflected light caused by the contents of a pattern.

As mentioned above, the light intensity of each pulse of pulsed light is measured at the TDI sensor side in Embodiment 1, and at the light source side in Embodiment 2, being synchronized with the period of each pulsed light. For each pixel of the optical image, a pixel value output from the TDI sensor is corrected using a total light amount of each corresponding pulse. By such a correction, the output change of the TDI sensor can be corrected even when a pulsed light is used.

According to Embodiments 1 and 2, it is possible to correct the output change of the TDI sensor in the case of a pulsed light being used. Thus, a pulsed light source can be loaded in the inspection apparatus.

What is expressed by the term "unit" or "circuit" in the description above can be configured by computer programs. They may be implemented by software programs executed by the computer system. Alternatively, they may be executed by a combination of hardware and software, or a combination of hardware and firmware. When constituted by a program, the program is stored in a computer readable recording medium, such as the magnetic disk drive 109, magnetic tape drive 115, FD 116, or ROM (Read Only Memory). For example, each circuit, etc. in the autoloader control circuit 113, the table control circuit 114, the reference circuit 112, the comparison circuit 108 and the position circuit 107 which constitute a calculation control unit may be configured by an electric circuit. Alternatively, they may be executed as software to be processed by the control computer 110, or executed by a combination of electric circuits and software.

While the embodiments have been described with reference to specific examples, the present invention is not limited thereto. For example, the inspection apparatus using a transmission optical system and a transmission light transmitted through the photomask 101 has been described in the above explanation, but the present invention is also effective to an inspection apparatus using a reflection optical system and a reflection light reflected from the photomask 101.

While description of the apparatus structure, control method, etc. not directly required for explaining the present invention is omitted, some or all of them may be suitably selected and used when needed. For example, although the structure of the control unit for controlling the inspection apparatus 100 is not described, it should be understood that a necessary control unit structure is to be selected and used appropriately.

In addition, any other pattern inspection apparatus and pattern inspection method that include elements of the present invention and that can be appropriately modified by those skilled in the art are included within the scope of the present invention.

Additional advantages and modification will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. A pattern inspection apparatus comprising:
a pulsed light source configured to emit pulsed light;
a stage configured to mount thereon an inspection target object with a pattern formed thereon;
a time delay integration (TDI) sensor configured to detect, a plurality of times with a time delay, each pixel value of an optical image of the inspection target object, wherein the optical image is acquired by emitting the pulsed light onto the inspection target object, and to integrate a detected each pixel value for each pixel of the optical image;
a light quantity sensor configured to detect a light quantity of the pulsed light having transmitted through or having been reflected by the inspection target object after emitting the pulsed light onto the inspection target object;
a light quantity measurement circuit configured to input the light quantity detected by the light quantity sensor, and to measure a light quantity of each pulse while being synchronized with a period of the pulsed light;
a correction unit configured to input the light quantity of each pulse and an integrated pixel value output from the TDI sensor, and to correct the integrated pixel value output from the TDI sensor, for each pixel of the optical image, by multiplying the integrated pixel value by a ratio between a reference total light quantity calculated using a reference image based on a design pattern data and a total light quantity of the light quantity of each corresponding pulse; and
an inspection unit configured to inspect whether there is a defect of the pattern, using the integrated pixel value corrected.

2. The apparatus according to claim 1, wherein the total light quantity is made to be variable by making a number of pulses of the each pixel value detected by the TDI sensor variable.

3. The apparatus according to claim 1, wherein a number of pulses of the light quantity used for the total light quantity is an integral multiple of a number of pixel values integrated by the TDI sensor.

4. A pattern inspection method comprising:

emitting pulsed light;

detecting, a plurality of times with a time delay, each pixel value of an optical image of an inspection target object with a pattern formed thereon, wherein the optical image is acquired by emitting the pulsed light onto the inspection target object, and integrating a detected each pixel value for each pixel of the optical image, by using a time delay integration (TDI) sensor;

detecting a light quantity of the pulsed light having transmitted through or having been reflected by the inspection target object after emitting the pulsed light onto the inspection target object;

inputting the light quantity detected and measuring a light quantity of each pulse while being synchronized with a period of the pulsed light;

inputting the light quantity of each pulse and an integrated pixel value output from the TDI sensor, and correcting the integrated pixel value output from the TDI sensor, for each pixel of the optical image, by multiplying the integrated pixel value by a ratio between a reference total light quantity calculated using a reference image based on a design pattern data and a total light quantity of the light quantity of each corresponding pulse; and inspecting whether there is a defect of the pattern, using the integrated pixel value corrected.

\* \* \* \* \*